United States Patent [19]

Hayashi et al.

[11] Patent Number: 4,925,861
[45] Date of Patent: May 15, 1990

[54] CARBOXYSTYRENE DERIVATIVES AND DRUGS CONTAINING THEM AS EFFECTIVE INGREDIENTS

[75] Inventors: Yoshio Hayashi; Oguri Tomei, both of Ushiku; Masaki Shinoda, Ami; Kazuo Takahashi, Komae; Munehiro Hashimoto, Machida, all of Japan

[73] Assignee: Mitsubishi Kasei Corporation, Tokyo, Japan

[21] Appl. No.: 181,156

[22] Filed: Apr. 13, 1988

[30] Foreign Application Priority Data

Apr. 16, 1987 [JP] Japan .................................. 62-93797

[51] Int. Cl.⁵ .................... A61K 31/38; C07D 277/24; C07D 277/64
[52] U.S. Cl. ...................... 514/367; 514/365; 544/335; 544/353; 544/354; 544/355; 544/356; 548/178; 548/180; 548/204; 548/333; 548/342; 546/168; 546/169; 546/170; 546/171; 546/174; 546/175
[58] Field of Search ....................... 548/180, 178, 204; 514/365, 367

[56] References Cited

U.S. PATENT DOCUMENTS 3,137,655 6/1964 Taul ................................... 252/301.2
3,974,282 8/1976 Engel et al. .

FOREIGN PATENT DOCUMENTS 0219308 4/1987 European Pat. Off. .
0219436 4/1987 European Pat. Off. .
0228959 7/1987 European Pat. Off. .
1576989 8/1969 France .
1473704 5/1977 United Kingdom .

OTHER PUBLICATIONS

Hayashi, et al., "Chemical Abstracts," vol. 110, 1989, col. 110:154289c.

*Primary Examiner*—Glennon Hollrah
*Assistant Examiner*—James H. Turnipseed
*Attorney, Agent, or Firm*—Oblon, Spivak, McClelland, Maier & Neustadt

[57] ABSTRACT

According to the present invention, there are provided novel carboxystyrene derivatives of the general formula (I):

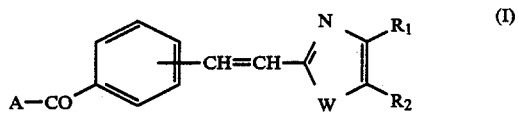

wherein the symbols are as defined hereinabove. Also provided herein are leukotriene antagonists and phospholipase inhibitors containing the carboxystyrene derivative or pharmaceutically acceptable salt thereof as an effective ingredient.

12 Claims, No Drawings

CARBOXYSTYRENE DERIVATIVES AND DRUGS CONTAINING THEM AS EFFECTIVE INGREDIENTS

BACKGROUND OF THE INVENTION

1. Field of the Invention:

The present invention relates to novel carboxystyrene derivatives and to leukotriene antagonists and phospholipase inhibitors containing said derivatives as effective ingredients. Description of the Prior Art:

There have been two methods for prophylactically or therapeutically treating allergic diseases.

One inhibits the release of substances mediating anaphylaxis. Representative drugs used for this purpose include disodium cromoglycate: *The Merck Index*, 9th Edition, 2585 (1976); and tranilast: *Nippon Yakuri Gakkai-shi* (Bulletin of Japanese Pharmacological Society), 74, 699 (1978).

The second method is to cause antagonists to act against the mediating substances released. Among drugs used in this method, e.g., diphenhydramine, chlorpheniramine, astemizole, terfenadine, clemastine, etc., which antagonize against histamine, one of substances mediating allergic reactions, have been well known.

It was suggested that certain substances which are not antagonized by antihistamic agents and are called slow reacting substances (SRS's) are released from the lung of patients of bronchial asthma: *Prog. Allergy*, 6, 539 (1962). "SRS" has recently been used as a general term for leukotriene $C_4$ ($LTC_4$), leukotriene $D_4$ ($LTD_4$) and leukotriene $E_4$ ($LTE_4$) *Proc. Natl. Acad. Sci. U.S.A.*, 76, 4275 (1979); *ibid.*, 77, 2014 (1980); and *Nature*, 285, 104 (1980). SRS has now been considered to be an important factor involved in human asthmatic ictus: *Proc. Natl. Acad. Sci. U.S.A.*, 80, 1712 (1983).

Some leukotriene antagonists have been known from patent or other publications. For example, FPL-55712 represented by the following formula:

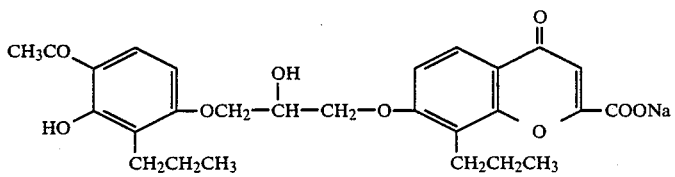

is disclosed in *Agents and Actions*, 9, 133 (1979); KC-404 represented by the following formula:

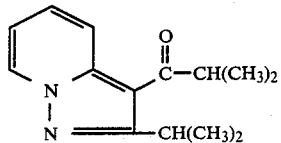

is disclosed in *Jap. J. Pharm.*, 33, 267 (1983); ONO-1078 represented by the following formula:

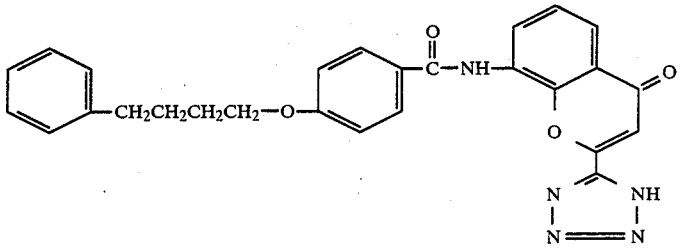

is disclosed in *Yuki Gosei Kagaku* (Organic Synthetic Chemistry), 45(2), 136 (1987); and LY-171883 represented by the following formula:

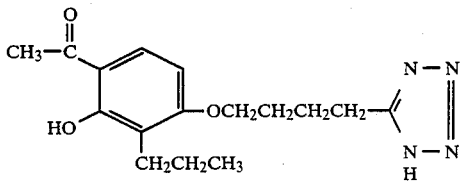

is also disclosed in *J. pharmacol. Exp. Ther.*, 233(1), 148 (1985).

However, no practical use of such antagonists has been reported.

Certain compound which resemble the compounds according to the present invention in chemical structure have also known. For example, the compound represented by the following formula:

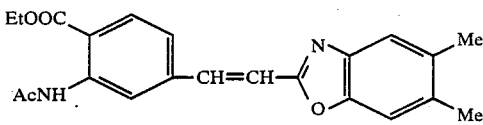

is described in German Pat. Publication (Offenlegungsschrift) No. 2,331,444; and the compound represented by the following formula:

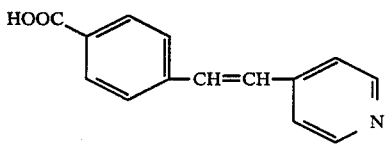

is also described in *J. Prakt. Chem.*, 6, 72 (1958). However, the leukotriene antagonizing activity of such compounds is not disclosed therein.

SUMMARY OF THE INVENTION

The present inventors have searched for compounds which have an antagonistic activity against leukotrienes and therefore are effective as drugs for therapeutically treating various diseases caused by the leukotrienes, and finally found that certain novel carboxystyrene derivatives have not only an excellent leukotriene-antagonistic activity but also a phospholipase-inhibiting activity. Thus, the present invention have now been attained.

Phospholipase A2 affects phosphatidylcholines to release arachidonic acid. Through the metabolic pathway called arachidonate cascade, the arachidonic acid may be converted, on the one hand, by the action of cyclooxygenase into prostaglandins (PGs) associated with inflammation and further into thromboxane $A_2$ ($TXA_2$) causing platelet agglutination and vasoconstriction and, on the other hand, it may be metabolized by the action of lipoxygenase into the aforementioned mediators $LTC_4$, $LTD_4$ and $LTE_4$ of allergic reactions and into $LTB_4$ associated with inflammation.

Accordingly, because of their phospholipase inhibiting activity, the carboxystyrene derivatives of the present invention will also be effective in the prophylactic and/or therapeutic treatment of such diseases caused by metabolites from arachidonic acid as, for example, inflammation, rheumatoid arthritis, cardiac infarction, asthma, etc.

It is an object of the present invention to provide novel carboxystyrene derivatives as specifically defined hereinbelow, which have a phospholipase inhibiting activity as well as an excellent leukotriene antagonistic activity.

Another object of the invention is to provide leukotriene antagonists and phospholipase inhibitors, which contain said novel carboxystyrene derivatives of the present invention as effective ingredients.

Other objects will be apparent from the detailed description which follows.

DESCRIPTION OF THE INVENTION

According to the present invention, there are provided carboxystyrene derivatives represented by the following general formula (I):

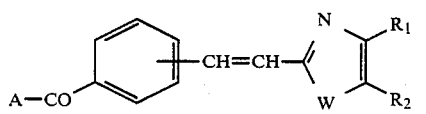

wherein:
A represents a hydroxyl group,
an alkoxy group having 1 to 5 carbon atoms,
a group represented by the formula:

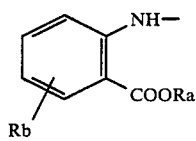

wherein $R_a$ is a hydrogen atom or a linear or branched alkyl group having 1 to 5 carbon atoms, m is an integer of 0 to 2 inclusive, and each of $R_3$ and $R_4$ is independently a hydrogen atom or a linear or branched alkyl group having 1 to 5 carbon atoms, or $R_3$ and $R_4$ may together form a cyclopentane or cyclohexane ring, or a group represented by the formula:

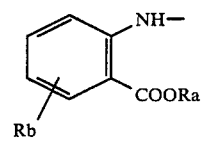

wherein $R_a$ is as defined above, and $R_b$ is a hydrogen atom, a halogen atom, a carboxyl group, a linear or branched alkyl group having 1 to 5 carbon atoms, an alkoxy group having 1 to 5 carbon atoms, an alkoxycarbonyl group having 2 to 6 carbon atoms, an acyl group having 1 to 4 carbon atoms, a hydroxyl group, an amino group, an acylamino group having 1 to 3 carbon atoms, or a nitro group;

W represents a linking group containing 1 to 3 atoms, provided that W is not an oxygen atom alone; and each of $R_1$ and $R_2$ independently represents a hydrogen atom, a linear or branched alkyl group having 1 to 5 carbon atoms, a phenyl group which may have one or more substituents, an alkoxycarbonyl group having 2 to 6 carbon atoms, or a carboxyl group, or $R_1$ and $R_2$ may together form a butadienylene group represented by the formula:

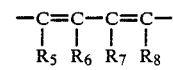

wherein each of $R_5$, $R_6$, $R_7$ and $R_8$ is independently a hydrogen atom, a halogen atom, a carboxyl group, a linear or branched alkyl group having 1 to 5 carbon atoms, an alkoxy group having 1 to 5 carbon atoms, an alkoxycarbonyl group having 2 to 6 carbon atoms, an acyl group having 1 to 4 carbon atoms, an amino group, an acylamino group having 1 to 3 carbon atoms, or a nitro group, provided that $R_1$ and $R_2$ together form the butadienylene group as defined above when W is —CH=CH—, and their pharmaceutically acceptable salts.

The carboxystyrene compounds of the present invention may preferably be represented by the above described general formula (I) wherein the benzene ring has the substituents in the meta position.

The present compounds of the general formula (I) described above will be illustrated hereinbelow in more detail. However, the scope of the compounds included in the general formula (I) is not limited to those illustrated hereinbelow.

Illustrative examples of alkoxy groups having 1 to 5 carbon atoms which may be represented by A, $R_b$, $R_5$, $R_6$, $R_7$ and $R_8$ in the general formula (I) may include methoxy, ethoxy, n-propoxy, iso-propoxy, n-butoxy, sec-butoxy, tertbutoxy, n-pentyloxy, iso-pentyloxy, tert-pentyloxy, etc.

Illustrative examples of linear or branched alkyl groups having 1 to 5 carbon atoms which may be represented by $R_a$, $R_b$, $R_1$, $R_2$, $R_3$, $R_4$, $R_5$, $R_6$, $R_7$ and $R_8$ may include methyl, ethyl, n-propyl, iso-propyl, n-butyl, sec-butyl, tert-butyl, n-pentyl, iso-pentyl, tert-pentyl, etc.

Illustrative examples of alkoxycarbonyl groups having 2 to 6 carbon atoms which may be represented by $R_b$, $R_1$, $R_2$, $R_5$, $R_6$, $R_7$ and $R_8$ may include methoxycarbonyl, ethoxycarbonyl, n-propoxycarbonyl, iso-propoxycarbonyl, n-butoxycarbonyl, tertbutoxycarbonyl, n-pentyloxycarbonyl, iso-pentyloxycarbonyl, etc.

Illustrative examples of acyl groups having 1 to 4 carbon atoms which may be represented by $R_b$, $R_5$, $R_6$, $R_7$ and $R_8$ may include formyl, acetyl, propionyl, butyryl, etc.

Illustrative examples of acylamino groups having 1 to 3 carbon atoms which may be represented by $R_b$, $R_5$, $R_6$, $R_7$ and $R_8$ may include formylamino, acetylamino, propionylamino, etc.

Illustrative examples of substituents of the substituted phenyl groups which may be represented by $R_1$ and $R_2$ may include halogen atoms such as chlorine, bromine and fluorine; hydroxyl group; alkoxy groups such as methoxy and ethoxy; alkoxycarbonyl groups such as methoxycarbonyl and ethoxycarbonyl; carboxyl group; amino group; acylamino groups such as acetylamino group; nitro group; cyano group; etc.

Illustrative examples of hetrocyclic rings represented by the formula:

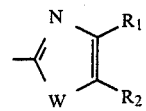

may include thiazole, benzthiazole, quinoline, quinoxaline, quinazoline, imidazole, benzimidazole, etc.

Among the compounds represented by the general formula (I) described above, those wherein the two substituents attached to the benzene ring are in meta position, the terminal substituents of the ethylenically double bond are entgegen isomeric each other, A is a group represented by the formula:

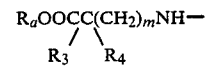

and the heterocyclic ring represented by the formula:

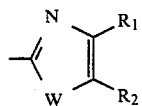

is thiazole or quinoline (that is, W is -S- or -CH=CH-) are preferred.

More preferable compounds of the present& invention are those wherein $R_a$ is hydrogen atom, each of $R_3$ and $R_4$ is a linear or branched alkyl group having 1 to 5 carbon atoms, and m is an integer having a value of one.

The carboxystyrene derivatives according to the present invention are not limited to specific isomers. Rather, they include all of geometrical and optical isomers and their mixtures, e.g., racemic bodies.

The carboxystyrene derivatives of the present invention may be prepared in various manners.

For example, the present derivatives may be prepared by the following reactions A-1 to A-4 and B-1 to B-2 shown in Reaction Scheme-1:

Reaction Scheme 1

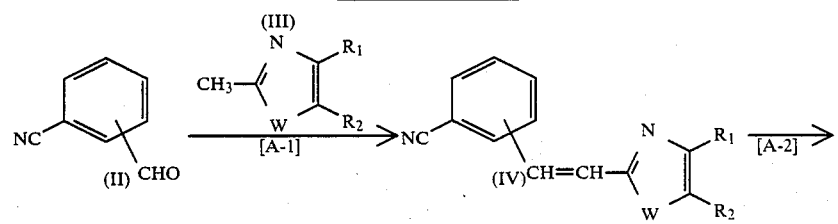

-continued
Reaction Scheme 1

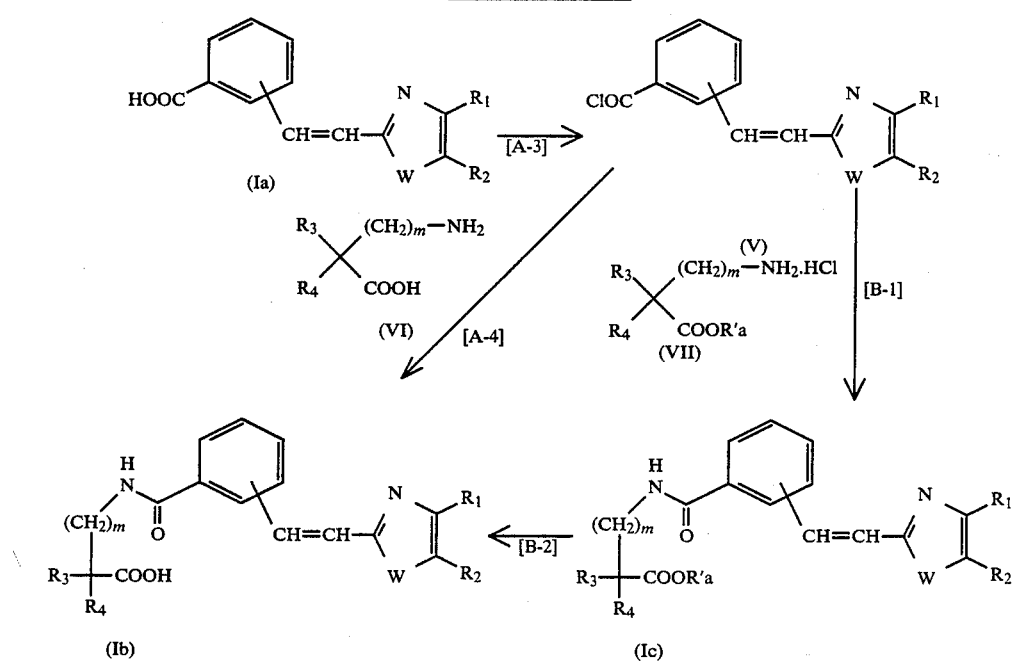

In Reaction Scheme-1, $R_1$ to $R_4$, W and m are as defined previously for the general formula (I), and $R_a'$ represents a linear or branched alkyl group having 1 to 5 carbon atoms.

In the synthetic route A, one equivalent of a cyanobenzaldehyde (II) is reacted with 0.8 to 2 equivalents of a compound (III) and 0.5 to 2 equivalents of acetic anhydride to produce a compound (IV) in Step A-1. This reaction may generally be carried out without use of any solvent, although it can be performed in a solvent which may be a high boiling point solvent such as xylene, dimethylformamide, dimethylsulfoxide and the like. Reaction temperatures may range from room temperature up to 250° C., preferably from 110 to 180° C.

In Step A-2, a compound (Ia) may easily be obtained in any conventional manner, for example, either by hydrolyzing the compound (IV) in a water-containing alcoholic solvent and in the presence of an inorganic alkali metal base such as sodium hydroxide, potassium hydroxide or potassium carbonate followed by treating with a mineral acid such as hydrochloric acid or sulfuric acid; or by hydrolyzing the compound (IV) directly with a mineral acid. The reaction may be carried out at temperatures in the range from room temperature to 200° C., preferably from room temperature to 120° C.

In Step A-3, a compound (V) may be obtained by reacting the compound (Ia) with a halogenating agent such as thionyl chloride or phosphorus oxychloride in a conventional manner. This reaction may be carried out in an aromatic hydrocarbon solvent such as benzene or toluene or a halogenated hydrocarbon solvent such as dichloroethane or chloroform. Reaction temperatures used herein range from 0° C. up to the boiling point of th solvent employed.

In Step A-4, a compound (Ib) is obtained by SchottenBaumann reaction in which the compound (V) is reacted with a compound (VI) in the presence of an inorganic base such as sodium hydroxide. Solvents which can be preferably employed in this reaction may include etheric solvents such as tetrahydrofuran, diethyl ether and dioxanes; aromatic hydrocarbon solvents such as toluene and benzene; and mixed solvents of a halogenated hydrocarbon solvent such as dichloromethane or chloroform with water. The reaction is carried out at temperatures in the range from 0° to 100° C., preferably from 0° C. up to room temperature.

Alternatively, the compound (V) is reacted with a compound (VII) in Step B-1, where conditions similar to those in Step A-4 are used, and the resulting compound (Ic) is then hydrolyzed in Step B-2 under conditions similar to those in Step A-2. Thus, the compound (Ib) can also be obtained. In this case, the hydrolysis under basic conditions may preferably be carried out in the presence of a catalytic amount of Triton B.

In the Reaction Scheme 1, the compound (Ia) can be esterified by any conventional manner to produce a compound of the general formula (I) wherein A is an alkoxy group having 1 to 5 carbon atoms. Further, the compound (VI) may be substituted by a compound represented by the following formula:

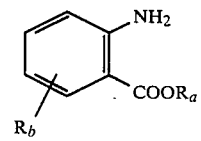

in Step A-4 to produce a corresponding compound of the general formula (I) wherein A is a group of the following formula:

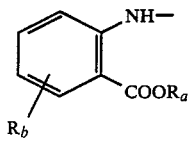

or alternatively, the just described compound may be obtained by replacing the compound (VII) with a compound represented by the following formula:

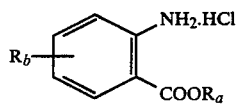

in the synthesis route B. The conditions for effecting these reactions are similar to those in Steps A-4 and B-1 and optionally B-2.

The compounds of the general formula (I) according to the present invention have significant leukotriene antagonistic and phospholipase $A_2$ inhibiting activities.

Thus, in vitro tests of the compounds according to the present invention for antagonistic activities against SRS using the ileum extracted from a guinea pig have revealed the selective antagonistic activity of the present compounds against SRS even in very low concentrations. Accordingly, the present compounds are effective in the prophylactic and/or therapeutical treatment of various diseases caused by leukotrienes, for example, allergic diseases such as asthma, brain edema and cerebral blood vessel contraction due to cerebral ischemia, or angina due to decrease of blood flow in the coronary vessel.

The compounds of the present invention also have inhibiting activity against phospholipase as shown in the method of Hendrickson et al., Anal. Biochem., 116, 553 (1981). Therefore, the present compounds are also effective in the prophylactic and/or therapeutical treatment of those diseases caused by arachidonic acid metabolites, such as $TXA_2$, PGs and leukotrienes, for example, inflammatory diseases, rheumatoid arthritis, cardiac infarction, etc.

The leukotriene antagonists and phospholipase inhibitors according to the present invention contain at least one compound of the general formula (I) or pharmaceutically acceptable salt thereof as an effective ingredient in association with at least one solid or liquid carrier or vehicle, and/or additive such as diluent, excipient, stabilizer or the like.

When the present compounds have one or more carboxyl groups, preferred salts herein may include pharmaceutically acceptable, non-toxic salts of alkali metals such as sodium and potassium, alkaline earth metals such as magnesium and calcium, and aluminum. Also preferably included herein are appropriate, non-toxic salts of amines such as ammonium, lower alkyl amines, e.g., triethylamine, hydroxy lower alkyl amines, e.g., 2-hydroxyethylamine, bis-(2-hydroxyethyl)amine, tris-(hydroxymethyl)aminomethan or N-methyl-D-glucamine, cycloalkyl amines, e.g., dicyclohexylamine, benzyl amines, e.g., N,N'-dibenzylethylenediamine, as well as dibenzyl amines. With respect to basic nitrogen-containing heterocyclic rings in the present compounds, preferred salts may include non-toxic hydrochloride, methanesulfonate, hydrobromide, sulfate, phosphate, fumarate, succinate salts. These salts are most suitable for use in injectable preparations since they are soluble in water.

The proportion of the therapeutically effective ingredient in said leukotriene antagonists may vary between 1% by weight and 90% by weight based on the carrier component(s).

The leukotriene antagonists or phospholipase inhibitors according to the present invention may be in any dosage form such as granule, parvule, powder, tablet, hard capsule, soft capsule, syrup, emulsion, suspension or solution for oral administration, or in the form of injectable solution for intravenous, intramuscular or subcutaneous administration. They may also be in other dosage form, such as suppository, collunarium, collyrium or inhalant, for rectal, nasal, ophthalmic or pulmonary, topical administration. They may also be formulated into powder for injection to be prepared in situ before use.

Organic or inorganic solid or liquid carriers or diluents or vehicles pharmaceutically suitable for peroral or enteral, parenteral or topical administration may be used to formulate the leukotriene antagonists or phospholipase inhibitors according to the present invention.

Excipients used to formulate solid preparations may include, for example, lactose, sucrose, starch, talc, cellulose, dextrin, kaolin, calcium carbonate and the like.

Liquid preparations for oral administration, such as emulsions, syrups, suspensions and solutions, may contain one or more generally used, inert diluents, such as water and vegetable oils. Such preparations can contain, in addition to the inert diluent(s), one or more adjuvants, such as humectants, suspending agents, edulcorants, flavors, colorants and preservatives. Liquid preparations may also be impregnated in capsules of absorbent materials such as gelatine.

Solvents and suspending agents used to formulate preparations for parenteral administration, such as injections, suppositories, collunaria, collyria and inhalants, may include, for example, water, propylene glycol, polyethylene glycols, benzyl alcohol, ethyl oleate, lecithins. Base materials used in suppositories may include, for example, cacao butter, emulsified cacao butter, laurin oil, Witepzol, etc.

These preparations may be prepared in any conventional manner.

When such preparations are orally administered, the amount of the compound according to the invention administered clinically may generally 0.01 to 1,000 mg, preferably 0.01 to 100 mg, per day to an adult. More preferably, such amounts may be varied as appropriate depending upon ages, symptoms and conditions of patients to be treated and presence or absence of concurrent administration. The daily amount of leukotriene antagonist or phospholipase inhibitor may be administered once a day, or twice or three times a day with an appropriate time interval. The drug of the present invention may also be administered intermittently.

When the drugs of the present invention are employed as injections, the compound of this invention may preferably be administered continuously or intermittently to an adult in an amount of 0.001 to 100 mg per once.

According to the present invention, there are provided novel carboxystyrene derivatives having remarkable leukotriene antagonistic and phospholipase inhibiting activities. The present carboxystyrene derivatives are useful for the prophylactic and therapeutic treatment of various diseases caused by leukotriene as leukotriene antagonists and those caused by the metabolites from arachidonic acid as phospholipase inhibitors.

EXAMPLES

The present invention will be hereinbelow illustrated in more detail by the following synthesis example showing the preparation of a reaction intermediate, practical examples and test example. These examples do not limit the scope of the present invention.

In the following examples, "IR" and "NMR" represent "infrared absorption spectrum" and "nuclear magnetic resonance spectrum", respectively; solvent proportions used in chromatography are expressed by volume; IR data in cm.$^{-1}$ were measured by KBr tablet method unless otherwise noted; solvents used in NMR measurement are shown in bracket; and NMR data are shown in $\delta$ (ppm).

The number assigned to each of the compounds in Examples corresponds to that shown for those described in Tables 1, 2, 3, 4 and 5.

SYNTHESIS EXAMPLE

Preparation of
2-(2-(3-cyanophenyl)ethenyl)-4-isopropylthiazole

3-Cyanobenzaldehyde (3.93 g, 30.0 mmol) was mixed with 4-isopropyl-2-methylthiazole (4.19 g, 30.0 mmol), and acetic anhydride (1.53 g, 15.0 mmol) was added. The mixture was heated under stirring at 170° C for 24 hours. After the reaction, acetic acid was distilled out under reduced pressure and the residue was purified by column chromatography (SiO$_2$, n-hexane/ethyl acetate=3/1) to afford the indicated compound (4.10 g) with a yield of 54%.

m.p. (° C.): 54–56,
IR (cm$^{-1}$): $\nu$=2230, 1510, 1410, 1235, 965.

EXAMPLE 1

Preparation of 3-(2-(2-benzthiazolyl))ethenylbenzoic acid (Compound No. 1)

2-(2-(3-Cyanophenyl)ethenyl)benzthiazole (3.00 g, 11.5 mmol) was dissolved in 50 ml of ethanol. After 10 ml of 30% aqueous potassium hydroxide solution was added, the resulting mixture was heated under reflux for 19 hours. The reaction mixture was cooled, neutralized with 5% hydrochloric acid, extracted with ethyl acetate, and dried. The solvent was then distilled out to produce a crude product. This crude crystal was washed with ether to afford the indicated compound (2.60 g) with a yield of 81%.

m.p. (° C.): 238–240,
IR (cm$_{-1}$): $\nu$=1690, 1440, 1260, 1195, 950.

EXAMPLE 2

Preparation of various benzoic acids

According to the procedures of Example 1, there were obtained the compounds Nos. 2, 3 and 4 shown in Table 1.

EXAMPLE 3

Preparation of
3-(2-(4-isopropyl-2-thiazolyl))ethenylbenzoic acid (Compound No. 5)

2-(2-(3-Cyanophenyl)ethenyl)-4-isopropylthiazole prepared in Synthetic Example (2.54 g, 10.0 mmol) was dissolved in a mixed solvent of acetic acid (5 ml) and concentrated hydrochloric acid (10 ml) and the resulting mixture was heated under stirring at 100° C. for 4 hours. After water was added, the reaction mixture was extracted with ethyl acetate and dried. The solvent was distilled out to afford the indicated compound (2.51 g) with a yield of 92%.

m.p. (° C.):185–186,
IR (cm$^{-1}$):$\nu$=1690, 1290, 1250, 950.

EXAMPLE 4

Preparation of
4-(N-(3-(2-(2-benzthiazolyl))ethenyl)benzoyl)aminobutyric acid (Compound No 6)

3-(2-(2-Benzthiazolyl)ethenyl)benzoic acid (Compound No. 2.30 g, 8.19 mmol) was suspended in 10 ml of toluene, and thionyl chloride (5.00 g, 42.0 mmol) was added. The resulting mixture was heated under reflux for 2 hours. Then, the solvent and excess thionyl chloride were distilled out under reduced pressure to produce a crude acid chloride. This crude product was suspended in 10 ml of dioxane. The resulting suspension was added to 30 ml of an aqueous solution containing gamma-aminobutyric acid (1.27 g, 12.3 mmol) and sodium hydroxide (1.00 g, 25.0 mmol) at 0° C. The reaction mixture was stirred for 2 hours and neutralized with dilute hydrochloric acid. The precipitated crystal was filtered and recrystalized from chloroform/methanol (1/1) to afford the indicated compound (1.82 g) with a yield of 61%.

m.p. (° C.): 211–212,
IR (cm$^{-1}$):$\nu$=1690, 1625, 1535, 1310, 1215, 950.

EXAMPLE 5

Preparation of various carboxystyrenes

According to the procedures of Example 4, there were obtained the compounds Nos. 7 to 13 shown in Table 1.

EXAMPLE 6

Preparation of ethyl 3-(N-(3-(2-(4 propyl-2-thiazolyl))ethenyl)benzoyl)amino-2,2-diethylpropionate (Compound No. 14)

The compound No. 2 (273 mg, 1.00 mmol) synthesized in Example 2 was suspended in 5 ml of toluene, and thionyl chloride (238 mg, 2.00 mmol) was added. The resulting mixture was heated under stirring at 80°

C. for 3.5 hours. The solvent and excess thionyl chloride were distilled out under reduced pressure to produce a crude chloride compound. The crude product was suspended in 5 ml of dioxane and added to 10 ml of an aqueous solution containing α,α-diethyl-β-alanine ethyl ester hydrochloride (251 mg, 1.20 mmol) and sodium hydroxide (240 mg, 6.00 mmol) at 0° C. The reaction mixture was stirred for 1.5 hours, extracted with ether and dried. The solvent was distilled out. The resulting crude product was purified by column chromatography (SiO2, hexane/ether=1/1) to afford the indicated compound (420 mg) with a yield of 98%.

IR (neat, cm$^{-1}$): $\nu$=1720, 1645, 1505, 1225, 1140,

NMR (CDCl$_3$):δ=6.7–8.0 (m, 7H), 4.18 (q, 2H, J=7 Hz), 2.78 (t, 2H, J=7 Hz), 2.69 (d, 2H, J=7 Hz), 1.5–2.1 (m, 6H), 1.28 (t, 3H, J=7 Hz), 0.90 (t, 6H, J=7 Hz).

EXAMPLE 7

Preparation of various alkoxycarboxylstyrenes

According to the procedures of Example 6, there were obtained the compounds Nos. 15 to 18 shown in Table 1.

Example 8

Preparation of 3-(N-(3-(2-(4-propyl-2-thiazolyl))ethenyl)benzoyl)amino-2,2-diethylpropionic acid (Compound No. 19)

Ethyl 3-(N-(3-(2-(4-propyl-2-thiazolyl))ethenyl)benzoyl)amino-2,2-diethylpropionate (Compound No. 14) synthesized in Example 6 (350 mg, 0.82 mmol) was dissolved in 5 ml of ethanol and 8 ml of 5% aqueous potassium hydroxide solution and three drops of Triton B were added. The mixture was heated under reflux for 3.5 hours. After the reaction, 2% dilute hydrochloric acid was added to acidify. The resulting product was extracted with ether and dried. The solvent was distilled out. The resulting crude product was purified by column chromatography (SiO$_2$, ether) to afford the indicated compound (113 mg) with a yield of 35%.

m.p. (° C.): 48–50,

IR (cm$^{-1}$):$\nu$=1700, 1630, 1510, 1225, 950.

EXAMPLE 9

Preparation of various carboxystyrenes

According to the procedures of Example 8, there were obtained the compounds Nos. 20 to 23.

EXAMPLE 10

Preparation of sodium 4-(N-(3-(2-(2-benzthiazolyl))ethenyl)benzoyl)aminobutyrate (Compound No 24)

4-(N-(3-(2-(2-benzthiazolyl))ethenyl)benzoylaminobutyric acid (Compound NO. 6, 1.50 g, 4.10 mmol) was dissolved in 30 ml of methanol. A solution of sodium hydrogencarbonate (344 mg, 4.10 mmol) dissolved in 5 ml of water was added at room temperature. The reaction mixture was heated under reflux for 1.5 hours. After the reaction, the solvent was distilled out and the product was recrystallized from ethanol to afford the indicated compound (1.45 g) with a yield of 91%.

m.p. (° C): 245–247,

IR (cm$^{-1}$):$\nu$=1630, 1550, 1430, 1310, 1185, 945.

Among the compounds shown in Table 1, the compounds Nos. 7, 19, 21, 22 and 23 are preferred with respect to the pharmacological activities. The compounds Nos. 21, 22 and 23 are especially preferred.

According to the procedures of Examples described above, the compounds shown in Table 2 below can be synthesized.

TABLE 1

A—CO—[phenyl]—CH=CH—B

| Compound No. | A | B | Position of Substitution | m.p. [°C.] | IR [cm$^{-1}$], NMR(CDCl$_3$) |
|---|---|---|---|---|---|
| 1 | HO— | [2-benzothiazolyl] | m | 238~240 | 1690, 1440, 1260, 1195, 950 |
| 2 | HO— | [4-propyl-2-thiazolyl] | m | 156~157 | 1685, 1520, 1450, 1195, 965 |
| 3 | HO— | [2-quinolyl] | m | 229~231 | 1690, 1595, 1505, 1200, 960, 740 |

TABLE 1-continued

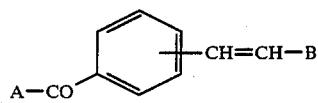

| Compound No. | A | B | Position of Substitution | m.p. [°C.] | IR [cm$^{-1}$], NMR(CDCl$_3$) |
|---|---|---|---|---|---|
| 4 | HO— | quinolin-2-yl | p | 295~300 | 1715, 1625, 1600, 1210, 745 |
| 5 | HO— | 4-isopropyl-2-methylthiazol-5-yl | m | 185~186 | 1690, 1290, 1250, 950 |
| 6 | HOOC(CH$_2$)$_3$NH— | benzothiazol-2-yl | m | 211~212 | 1690, 1625, 1535, 1310, 1215, 950 |
| 7 | HOOC-C(Me)$_2$-CH$_2$-NH— | benzothiazol-2-yl | m | 192~193 | 1695, 1625, 1525, 1155, 965 |
| 8 | HOOC(CH$_2$)$_2$NH— | 4-isopropyl-2-methylthiazol-5-yl | m | 175~176 | 1705, 1630, 1540, 1330, 1190 |
| 9 | HOOC-C(Me)$_2$-CH$_2$-NH— | 4-isopropyl-2-methylthiazol-5-yl | m | 151~152 | 1690, 1650, 1510, 1170, 950 |
| 10 | HOOC(CH$_2$)$_3$NH— | quinolin-2-yl | m | 245~247 | 1690, 1630, 1530, 1200, 820 |
| 11 | HOOC(CH$_2$)$_3$NH— | quinolin-2-yl | p | 224~225 | 1700, 1625, 1530, 1290, 835 |
| 12 | HOOC-CH(Me)-NH— | quinolin-2-yl | m | 103~106 | 1635, 1600, 1525, 1205, 820 |
| 13 | 2-(HOOC)C$_6$H$_4$NH— | benzothiazol-2-yl | m | 243~245 | 1675, 1585, 1530, 950, 750 |
| 14 | EtOOC-C(Et)$_2$-CH$_2$-NH— | 4-propyl-2-methylthiazol-5-yl | m | | 1720, 1645, 1505, 1225, 1140 (neat 6.7~8.0 (m, 7H), 4.18(q, 2H J=7Hz), 2.78 (t, 2H J=7Hz), 2.69(d, 2H J=7Hz), 1.5~2.1(m, 6H) 1.28(t, 3H J=7Hz), 0.90(t, 6H J=7Hz) |

TABLE 1-continued

A—CO—⟨C₆H₄⟩—CH=CH—B

| Compound No. | A | B | Position of Substitution | m.p. [°C.] | IR [cm⁻¹], NMR(CDCl₃) |
|---|---|---|---|---|---|
| 15 | EtOOC-C(Et)(Et)-CH₂-NH— | 2-methylbenzothiazol-yl | m | oil | 1715, 1640, 1520, 1220, 1135, 955<br>6.7–8.0(m, 10H), 4.17(q, 2H J=7Hz), 3.63(d, 2H J=6Hz),<br>1.69(q, 4H J=7Hz), 1.27(t, 3H J=J=7Hz), 0.90(t, 6H J=7Hz) |
| 16 | EtOOC-C(Et)(Et)-CH₂-NH— | 2-methyl-4-isopropylthiazol-5-yl | m | oil | 1715, 1635, 1445, 1225, 1140, 960<br>7.3~8.0(m, 6H), 6.80(s, 1H), 4.19(q, 2H J=7Hz)<br>3.65(d, 2H J=6Hz), 3.12(m, 1H), 1.68(q, 4H J=7Hz)<br>1.35(d, 6H J=7Hz), 1.30(t, 3H J=7Hz), 0.91(t, 6H J=7Hz) |
| 17 | EtOC(=O)-cyclohexyl-CH₂-NH— | 2-methyl-4-isopropylthiazol-5-yl | m | 105~106 | 1710, 1610, 1530, 1190, 1125, 955 |
| 18 | HOOC-C(Me)(CH₂CH(CH₃)₂)-CH₂-NH— | 2-methyl-4-isopropylthiazol-5-yl | m | oil | 1720, 1645, 1525, 1225, 1145, 960<br>6.8~8.1(m, 7H), 4.19(q, 2H J=7Hz), 3.62(d, 2H J=6Hz)<br>3.12(m, 1H), 1.5~1.7(m, 2H), 1.32(d, 6H J=7Hz), 1.27(s, 3H)<br>0.90(d, 6H J=6Hz) |
| 19 | HOOC-C(Et)(Et)-CH₂-NH— | 2-methyl-4-propylthiazol-5-yl | m | 48~50 | 1700, 1630, 1510, 1225, 950 |
| 20 | HOOC-C(Et)(Et)-CH₂-NH— | 2-methylbenzothiazol-yl | m | 202~204 | 1700, 1620, 1525, 1240, 1160, 960 |
| 21 | HOOC-C(Et)(Et)-CH₂-NH— | 2-methyl-4-isopropylthiazol-5-yl | m | 54~56 | 1690, 1620, 1500, 1220, 951 |
| 22 | HOOC-C(cyclohexyl)-CH₂-NH— | 2-methyl-4-isopropylthiazol-5-yl | m | 149~150 | 1720, 1610, 1540, 1190, 1130, 955 |
| 23 | HOOC-C(Me)(CH₂CH(CH₃)₂)-CH₂-NH— | 2-methyl-4-isopropylthiazol-5-yl | m | 138~139 | 1700, 1625, 1540, 1225, 1160, 960 |

TABLE 1-continued

A—CO—〔phenyl〕—CH=CH—B

| Compound No. | A | B | Position of Substitution | m.p. [°C.] | IR [cm$^{-1}$], NMR(CDCl$_3$) |
|---|---|---|---|---|---|
| 24 | NaOOC—CH$_2$CH$_2$CH$_2$—NH— | 2-methylbenzothiazole | m | 245~247 | 1630, 1550, 1430, 1310, 1185, 945 |

TABLE 2

A—CO—〔phenyl〕—CH=CH—B

| Compound No. | A | B | Position of Substitution |
|---|---|---|---|
| 25 | HOOC—C(Et)(Me)—CH$_2$—NH— | thiazole-COOMe | m |
| 26 | HOOC—CH(Me)—CH$_2$—NH— | thiazole-C$_6$H$_4$-Cl | m |
| 27 | 5-chloro-2-(NH—)benzoic acid | thiazole-C(CH$_3$)$_3$ | m |
| 28 | 6-methyl-2-(NH—)benzoic acid | thiazole-CH(CH$_3$)$_2$ | m |
| 29 | 2-(NH—)benzoic acid | thiazole-CH(CH$_3$)$_2$ | o |
| 30 | HOOC—C(Et)$_2$—CH$_2$—NH— | 2-(benzamide)-imidazoline | m |
| 31 | HOOC—C(Me)$_2$—CH$_2$—NH— | pyrimidine-C$_6$H$_4$-C$_5$H$_{11}$ | m |

TABLE 2-continued

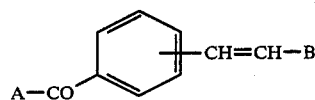

| Compound No. | A | B | Position of Substitution |
|---|---|---|---|
| 32 | isopentyl OOC-C(Et)(Et)-CH2-NH- | quinoxalin-2-yl | m |
| 33 | HOOC-C(Et)(Et)-CH2-NH- | 2-benzimidazolyl (1H) | m |
| 34 | HOOC-CH(pentyl)-CH2-NH- | 2-imidazolyl (1H) | m |
| 35 | HOOC-C(Et)(Et)-CH2-NH- | 2-(4-Pr-5-COOEt-thiazolyl) | m |
| 36 | HOOC-CH(Me)-NH- | 2-(4-tBu-thiazolyl) | m |
| 37 | HOOC-CH(isopentyl)-CH2CH2-NH- | 2-benzothiazolyl | m |
| 38 | 2-(COOH)-phenyl-NH- | 2-(4-C(CH3)3-5-COOH-thiazolyl) | m |
| 39 | 2-(COOH)-phenyl-NH- | 2-(4-Et-5-Me-thiazolyl) | m |
| 40 | 2-(COOH)-phenyl-NH- | 2-(2-(CONH-)phenyl-imino)methyl | m |
| 41 | 4-Cl-2-(COOH)-phenyl-NH- | quinazolin-2-yl | m |
| 42 | 4-MeO-2-(COOH)-phenyl-NH- | quinoxalin-2-yl | m |

TABLE 2-continued
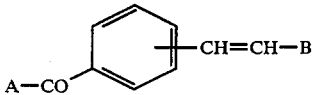
| Compound No. | A | B | Position of Substitution |
|---|---|---|---|
| 43 | 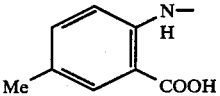 | 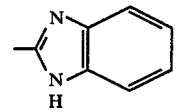 | m |
| 44 | 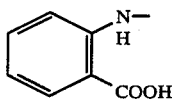 | 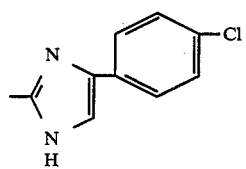 | m |
| 45 | 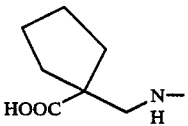 | 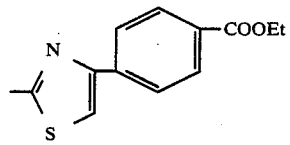 | m |
| 46 | 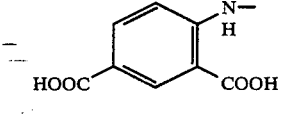 | 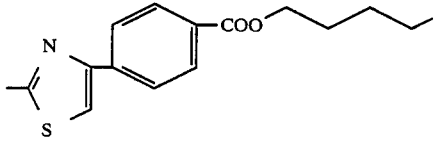 | m |
| 47 | 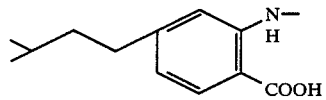 | 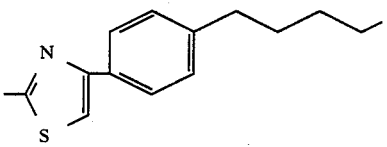 | m |
| 48 | 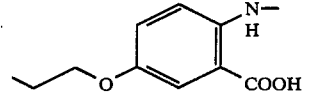 | 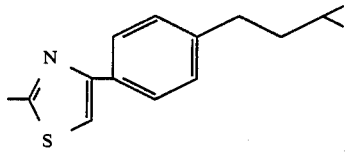 | m |
| 49 | 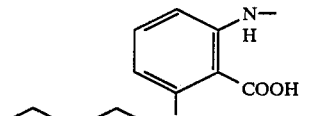 | 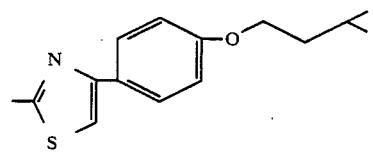 | m |
| 50 | 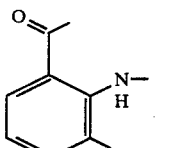 | 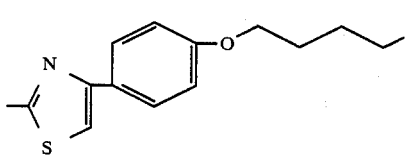 | m |

TABLE 2-continued $$A-CO-\langle\phantom{xxx}\rangle-CH=CH-B$$

| Compound No. | A | B | Position of Substitution |
|---|---|---|---|
| 51 | 2-(methylamino)-5-hydroxybenzoic acid | 2-(3-ethoxyphenyl)-thiazole | m |
| 52 | 4-propionamido-2-(methylamino)benzoic acid | 2-(2-propionylphenyl)-thiazole | m |
| 53 | 4-nitro-2-(methylamino)benzoic acid | 2-(4-propionamidophenyl)-thiazole | m |
| 54 | 3-methyl-3-carboxy-azetidine (Me, HOOC, N—H) | 2-methyl-4-(2-nitrophenyl)-5-butyl-thiazole | m |
| 55 | 2,2-diethyl-3-(methylamino)propanoic acid (Et, Et, HOOC, N—H) | 2-methyl-5-hexyl-thiazole | m |
| 56 | 2,2-dimethyl-3-(methylamino)propanoic acid (Me, Me, HOOC, N—H) | 2-methyl-4,5-dimethyl-thiazole | m |
| 57 | 2-methyl-3-(methylamino)propanoic acid (Me, HOOC, N—H) | 2-methyl-6-chloro-benzothiazole | m |
| 58 | 2,2-dimethyl-3-(methylamino)propanoic acid (Me, Me, HOOC, N—H) | 2-methyl-6-amino-benzothiazole | m |
| 59 | 3-(methylamino)propanoic acid (HOOC, N—H) | 2-methyl-6-formamido-benzothiazole | m |
| 60 | 2,2-dimethyl-3-(methylamino)propanoic acid (Me, Me, HOOC, N—H) | 2-methyl-4-(n-propoxycarbonyl)-benzothiazole | m |

TABLE 2-continued

A—CO—[phenyl]—CH=CH—B

| Compound No. | A | B | Position of Substitution |
|---|---|---|---|
| 61 | HOOC-CH(propyl)-CH2-NH- | 2-methyl-6-nitrobenzothiazol-yl | m |
| 62 | HOOC-C(Me)2-CH2-NH- | 2-methyl-6-methoxybenzothiazol-yl | m |
| 63 | HOOC-C(Me)2-CH2-NH- | 2-methyl-6-(isopentyloxy)benzothiazol-yl | m |
| 64 | HOOC-C(Me)2-CH2-NH- | 2-methyl-4-acetylbenzothiazol-yl | m |
| 65 | HOOC-C(Me)2-CH2-NH- | 2-methyl-6-(isopentyl)benzothiazol-yl | m |
| 66 | EtOOC-C(Et)2-CH2-NH- | benzothiazol-2-yl | m |
| 67 | 2-(ethoxycarbonyl)phenyl-NH- | 5-(tert-butyl)-4-carboxythiazol-2-yl | m |
| 68 | 4-chloro-2-(isopentyloxycarbonyl)phenyl-NH- | quinazolin-2-yl | m |
| 69 | 1-(HOOC)cyclohexyl-CH2-NH- | 4-(4-carboxyphenyl)thiazol-2-yl | m |
| 70 | 4-amino-2-(COOH)phenyl-NH- | 4-(2-acetylphenyl)thiazol-2-yl | m |

TABLE 2-continued $$\text{A—CO} \underset{\phantom{xxxxx}}{\overset{\phantom{xxxxx}}{\bigcirc}} \text{—CH=CH—B}$$

| Compound No. | A | B | Position of Substitution |
|---|---|---|---|
| 71 | HOOC–CH(CH₃)–NH– | 2-methyl-benzothiazol-4-yl-COOH | m |
| 72 | isobutyl–CH₂–CH₂–O– | 4-isopropyl-2-methyl-thiazol-5-yl | m |
| 73 | n-pentyl–O– | benzothiazol-2-yl | m |

EXAMPLE 11

Formulation of tablet preparations

Well pulverized 3-(N-(3-(2-(4-isopropyl-2-thiazolyl)-)ethenyl)benzoyl)amino-2-isobutyl-2-methylpropionic acid (Compound No. 23; 1,000 g), lactose (5,900 g), crystalline cellulose (2,000 g), hydroxypropylcellulose having a low substitution degree (1,000 g), and magnesium stearate (100 g) were thoroughly mixed and tabletted by direct tabletting method into base tablets containing 10 mg of the compound per tablet (100 mg). The base tablets were coated with sugar or film to prepare sugar- or film-coated tablets.

EXAMPLE 12

Formulation of capsule preparations

Well pulverized 2,2-diethyl-3-(N-(3-(2-(4-isopropyl-2thiazolyl))ethenyl)benzoyl)aminopropionic acid (Compound No. 21; 1,000 g), corn starch (3,000 g), lactose (6,900 g), crystalline cellulose (1,000 g), and magnesium stearate (100 g) were admixed to prepare capsules containing 10 mg of the compound per capsule (120 mg).

EXAMPLE 13

Formulation of inhalants

Well pulverized 3-(N-(3-(2-(4-isopropyl-2-thiazolyl)-)ethenyl)benzoyl)amino-2-spiro-1'-cyclohexanepropionic acid (Compound No. 22; 5 g), medium chain saturated fatty acid triglyceride (10 g), and sorbitan monooleate (0.2 g) were thoroughly mixed. The resulting admixture was packed into an aluminum bomb of 5 ml for aerosol in an amount of 15.2 mg per bomb. Each bomb was filled with 84.8 mg of freon 12/114 (1:1 mixture) at low temperature. A quantitative adapter of 100 µl per spray was attached to each bomb. Thus, inhalants for quantitative spray was prepared containing 5 mg of the compound per bomb (5 ml).

EXAMPLE 14 in vitro SRS antagonistic activity

The terminal ileum was taken from a male Hartley guinea pig (200 to 450 g) and the lumen was washed. The ileum was set in 5 ml of a tissue bath containing Tyrode's solution: NaCl 136 mM, KCl 2.7 mM, NaHCO$_3$ 11.9 mM, MgCl$_2$ 1.05 mM, CaCl$_2$ 1.8 mM, NaH$_2$PO$_4$ 0.4 mM, and glucose 5.6 mM. The temperature in the bath was kept at 37° C. and the bath was aerated by 95% oxygen/5% carbon dioxide. The buffer solution also contained $10^{-7}$ g/ml mepyramine and $5 \times 10^{-8}$ g/ml atropine in order to prevent the contraction caused by histamine and acetylcholine. Isometric measurement was done by an isotonic transducer (TD-112S, NIPPON KODEN, Japan) and change of tension in gram was recorded in a recticorder (RTG-4124, NIPPON KODEN, Japan). A tension of 0.5 g was passively loaded on the ileum. Thus, the contraction response of the ileum to SRS extracted from guinea pig lung was observed. The tonic contraction corresponding to one unit of SRS which corresponded to 5 ng of histamine was used as control. Varying concentrations of each compound to be tested were added to the tissue bath. The concentration of each compound to be tested which reduced the contraction of the control by 50%, IC$_{50}$, was shown as a minimal effective concentration in M in Table 3.

TABLE 3

| Compound No. | Anti-SRS Activity (Minimal Effective Concentration, M) |
|---|---|
| 1 | $2 \times 10^{-7}$ |
| 2 | $2 \times 10^{-8}$ |
| 3 | $5 \times 10^{-8}$ |
| 5 | $5 \times 10^{-8}$ |
| 6 | $10^{-5}$ |
| 7 | $5 \times 10^{-8}$ |

TABLE 3-continued

| Compound No. | Anti-SRS Activity (Minimal Effective Concentration, M) |
|---|---|
| 9 | $5 \times 10^{-8}$ |
| 10 | $5 \times 10^{-7}$ |
| 12 | $2 \times 10^{-7}$ |
| 19 | $2 \times 10^{-7}$ |
| 20 | $5 \times 10^{-8}$ |
| 21 | $5 \times 10^{-9}$ |
| 22 | $10^{-9}$ |
| 23 | $2 \times 10^{-10}$ |
| 24 | $10^{-5}$ |

Example 15 in vitro phospholipase inhibiting activity

In 2.4 ml of 5 mM tris(hydroxymethyl)aminomethane hydrochloride buffer (pH 8.0) containing 0.1M sodium chloride and 5 mM calcium chloride, 0.3 ml of a phospholipase $A_2$ solution from Naja mocambique or Porcine pancreas (Sigma) in a final concentration of 0.014 units per 0.01 μg per ml was preincubated with 0.03 ml of an inhibitor at 25° C. for 15 minutes. A synthetic substrate DPybPC, 1,2-bis(4-(1-pyreno)butyryl)-syn-glycero-3-phosphorylcholine (0.3 ml, final concentration: 2 μM) was added and incubation was continued for 30 minutes. The reaction was terminated by addition of hydrochloric acid (1N, 0.5 ml), the fluorescence intensity was measured (Ex. 332 nm; Em. 382 nm) to calculate the activity of the phospholipase $A_2$. The enzymes, synthetic substrate and inhibitor used were dissolved or diluted in the buffer. The results are shown in Table 4.

TABLE 4

| Compound No. | Phospholipase $A_2$ Inhibition (%) | Concentration of Compound to be Tested (M) |
|---|---|---|
| 13 | 73[a] | $10^{-5}$ |
| 20 | 47[a] | $10^{-5}$ |
| 22 | 74[b] | $10^{-5}$ |

[a] Phospholipase $A_2$ from Naja mocambique
[b] Phospholipase $A_2$ from Porcine Pancreas

TEST EXAMPLE

Acute toxicity

A suspension of the compound according to the present invention in 1% tragacanth solution was orally administered to a group of 4 to 5 ddy male mice of 6 week old. The mice were observed for 7 days to determine the number of dead animals. The results are shown in Table 5.

TABLE 5

| Compound No. | Acute Toxicity(LD$_{50}$ mg/kg) |
|---|---|
| 7 | > 700 |
| 19 | >1,000 |

What is claimed is:

1. A carboxystyrene represented by the formula (I):

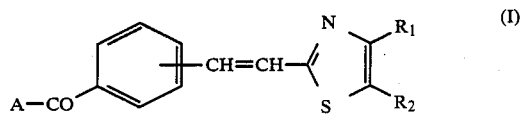

wherein:
A represents
a hydroxyl group,
an alkoxy group having 1 to 5 carbon atoms,
a group represented by the formula:

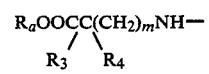

wherein $R_a$ is a hydrogen atom or a linear or branched alkyl group having 1 to 5 carbon atoms, m is an integer of 0 to 2 inclusive, and each of $R_3$ and $R_4$ is independently a hydrogen atom or a linear or branched alkyl group having 1 to 5 carbon atoms, and $R_3$ and $R_4$ may together form a cyclopentane or cyclohexane ring, or a group represented by the formula:

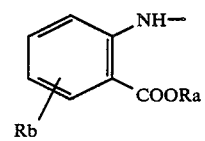

wherein $R_a$ is as defined above, and $R_b$ is a hydrogen atom, a halogen atom, a carboxyl group, a linear or branched alkyl group having 1 to 5 carbon atoms, an alkoxy group having 1 to 5 carbon atoms, an alkoxycarbonyl group having 2 to 6 carbon atoms, an acyl group having 1 to 4 carbon atoms, a hydroxyl group, an amino group, an acylamino group having 1 to 3 carbon atoms, or a nitro group;

and each of $R_1$ and $R_2$ independently represents a hydrogen atom, a linear or branched alkyl group having 1 to 5 carbon atoms, a phenyl group which may have one or more substituents, an alkoxycarbonyl group having 2 to 6 carbon atoms, or a carboxyl group, or $R_1$ and $R_2$ may together form abutadienylene group represented by the formula:

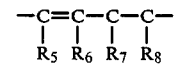

wherein each of $R_5$, $R_6$, $R_7$ and $R_8$ is independently a hydrogen atom, a halogen atom, a carboxyl group, a linear or branched alkyl group having 1 to 5 carbon atoms, an alkoxy group having 1 to 5 carbon atoms, an alkoxycarbonyl group having 2 to 6 carbon atoms, an acyl group having 1 to 4 carbon atoms, an amino group, an acylamino group having 1 to 3 carbon atoms, or a nitro group or a pharmaceutically acceptable salt thereof.

2. The compound of claim 1, wherein the substitutions of the benzene ring in the general formula (I) are in meta position.

3. The compound of claim 2 wherein A is

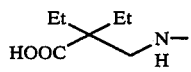

R₁ is isopropyl, and R₂ is hydrogen.

4. The compound of claim 2 wherein A is

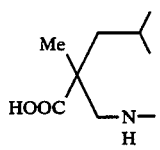

R₁ is isopropyl, and R₂ is hydrogen.

5. The compound of claim 2 wherein A is

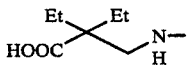

R₁ is propyl, and R₂ is hydrogen.

6. The compound of claim 2 wherein A is

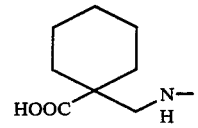

R₁ is isopropyl, and R₂ is hydrogen.

7. The compound of claim 2 wherein A is

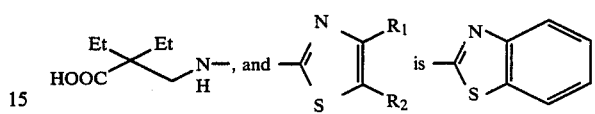

8. A pharmaceutical composition which is a leukotriene antagonist or a phospholipase inhibitor comprising an effective amount of a compound of claim 1 in a pharmaceutically acceptable carrier or excipient.

9. A pharmaceutical composition which is a leukotriene antagonist or a phospholipase inhibitor comprising an effective amount of a compound of claim 2 in a pharmaceutically acceptable carrier or excipient.

10. A pharmaceutical composition which is a leukotriene antagonist or a phospholipase inhibitor comprising an effective amount of a compound of claim 3 in a pharmaceutically acceptable carrier or excipient.

11. A method of antagonizing leucotrienes in a subject requiring such treatment which comprises administering to the subject a leucotriene antagonizing effective amount of a compound of claim 1.

12. A method of inhibiting phospholipase in a subject requiring such treatment which comprises administering to the subject a phospholipase inhibiting amount of a compound of claim 1.

* * * * *

UNITED STATES PATENT AND TRADEMARK OFFICE
CERTIFICATE OF CORRECTION

PATENT NO.　　:　　4,925,861

DATED　　　　:　　MAY 15, 1990

INVENTOR(S) :　　YOSHIO HAYASHI ET AL.

It is certified that error appears in the above-identified patent and that said Letters Patent is hereby corrected as shown below:

On the title page, item [75]:
    In the inventors, delete "Oguri Tomei" and insert --Tomei Oguri--.

Signed and Sealed this

Eleventh Day of June, 1991

Attest:

HARRY F. MANBECK, JR.

Attesting Officer

Commissioner of Patents and Trademarks